United States Patent [19]

Haber

[11] 4,036,945

[45] July 19, 1977

[54] COMPOSITION AND METHOD FOR DETERMINING THE SIZE AND LOCATION OF MYOCARDIAL INFARCTS

[75] Inventor: Edgar Haber, Weston, Mass.

[73] Assignee: The Massachusetts General Hospital, Boston, Mass.

[21] Appl. No.: 682,483

[22] Filed: May 3, 1976

[51] Int. Cl.² .................... A61K 29/00; A61K 43/00; G01T 1/161; G21H 5/02
[52] U.S. Cl. ..................................... 424/1; 128/2 A; 424/9; 250/303
[58] Field of Search .................... 424/1, 1.5, 9, 12, 85; 128/2 A; 250/303

[56] References Cited

U.S. PATENT DOCUMENTS 3,812,245  5/1974  Dugan ..................................... 424/1

OTHER PUBLICATIONS

Holman et al., Chemical Abstracts, vol. 79, No. 21, Nov. 26, 1973, p. 135, Abstract No. 123118h.
Willerson et al., Chemical Abstracts, vol. 83, No. 3, July 21, 1975, p. 219, Abstract No. 24383s.

*Primary Examiner*—Benjamin R. Padgett
*Assistant Examiner*—Christine M. Nucker

[57] ABSTRACT

Radioactive labelled antibody for cardiac myosin is injected intravenously after cardiac occlusion and is specifically absorbed in infarcted myocardium, as are radioactive labelled lower molecular weight fragments of the antibody such as (Fab')$_2$, (Fab'), and (Fv). The location and size of the myocardial infarct can be determined by measuring the intensity and location of radioactive emission externally of the heart.

6 Claims, 4 Drawing Figures

COMPOSITION AND METHOD FOR DETERMINING THE SIZE AND LOCATION OF MYOCARDIAL INFARCTS

The invention described herein was made in the course of work under a grant or award from the Department of Health, Education and Welfare.

This invention relates to a process of determining the location and size of myocardial infarcts without the need for surgery and to a composition comprising a radioactive labelled antibody for cardiac myosin or radioactive labelled lower molecular weight fragments of such antibody useful in such process.

It has previously been proposed to determine location and size of acute myocardial infarcts by injecting into the bloodstream radiopharmaceuticals which are selectively sequestered in the area of myocardial damage. The radiopharmiaceuticals used have included $^{203}$Hg-chlormerodrin by Gorten et al., Am. Heart J. Vol. 72 (1966); $^{203}$Hg-mercurifluorescein by Hubner, Cardiovasc. Res. Vol 4, 509 (1970); $^{167}$Ga-citrate by Kramer et al.; and $^{99m}$Tc-labelled materials by Bonte et al., Radiology Vol. 110, 473 (1974), Holman et al., N. Engl. J. Med. Vol. 291, 159 (1974), and Rossman et al., J. Nucl. Med. Vol. 16, (1975). These procedures have produced relatively poor definition because of non-specific absorption of the radiolabelled materials by other tissues. It has also been proposed to use fluoresceine labelled antibodies to detect or localize cell membrane antigens as proposed by Lender et al., J. Exp. Med. Vol. 142, 41–49 (1975), as well as cell membrane bound immunoglobulins (Zucker-Franklin J. Exp. Med., Vol. 135, pages 533–548 (1972)), and to delineate intracellular structural components (Lazarides et al., Proc. Nat. Acad. Sci. (U.S.A.) Vol. 71, pages 2268–2272 (1974)).

It has now been found that following coronary occlusion intravenous injection of antibody specific for cardiac myosin or of lower molecular weight fragments thereof such as the fragments identified as (Fab')$_2$, (Fab'), and (Fv) leads to localization and concentration of the antibody or fragment in the zone of ischemic damage resulting from myocardial infarction. Surprisingly, the antibody or antibody fragment uptake is greatest in regions of the myocardial tissue where blood flow is most severely reduced. The highly specific absorption makes possible good definition of the infarction by external counting when the antibody or fragment is suitably labelled with a radioactive isotope even when a quantity of antibody protein or fragment as small as 10–250 μg is injected. Preferably, the amount of antibody or fragment injected is less than 100 μg of protein in order to minimize possible allergic reaction.

Figure 1:
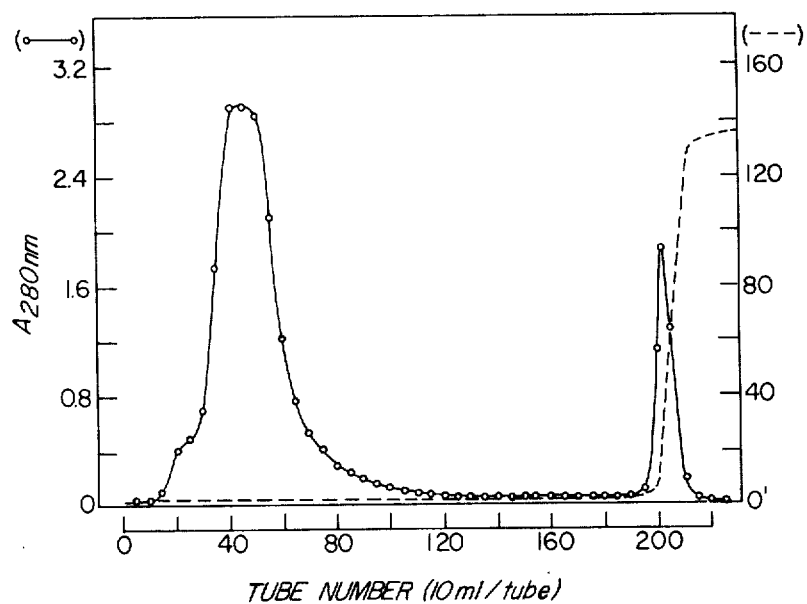
FIG. 1 is a graphical representation of the elution profile of antibody for canine cardiac myosin purified by affinity chromatography on a myosin-agarose column, elution being by means of 5 molar guanidine hydrochloride, elution of which is shown by rise in conductivity.

The antibody, a protein having a molecular weight of approximately 225,000, can be prepared by conventional procedures by injecting purified cardiac myosin into a suitable host animal, then bleeding the animal and concentrating the antiserum. Cardiac myosin can be isolated by the procedure of Kantz et al., Circ. Res. Vol. 19, pages 611–620 (1965) and further purified by precipitation with 37–42% saturated ammonium sulfate as described by Wikman-Coffelt et al., Biochem. Biophys. Res. Commun. Vol. 51, No. 4, pages 1097–1104 (1973), followed by dialysis and centrifugation. The purified cardiac myosin emulsified in complete Freund's adjuvant is then injected at suitable intervals into a selected animal such as rabbit, sheep or horse, after which the animal is bled, the antiserum separated by clotting, and the antibody further purified by ammonium sulfate precipitation, centrifugation, dialysis, and affinity chromatography in a column containing cardiac myosin bonded to a solid support such as agarose. The solution of antibody thus obtained can be concentrated if desired by vacuum dialysis to provide a solution containing from 0.5 to 5 mg/ml.

The antibody for cardiac myosin thus purified can be fragmented by conventional procedures to provide lower molecular weight fragments which are preferred for use in the present invention. The antibody can be fragmented with pepsin, by the procedure described by Edelman et al. in Methods in Immunonology and Immunochemistry, Vol. 1, pages 422–423 (Academic Press, 1967) to produce (Fab')$_2$ fragments having a molecular weight of about 100,000. The purified (Fab')$_2$ can be fragmented further by the reduction with mercaptoethanol to produce (Fab') fragments having a molecular weight of about 50,000 as described in the same publication. The purified antibody can also be fragmented by a variation of the procedure of Hochman et al., Biochemistry, Volume 12, pages 1130–1135, (1973), to produce (Fv) fragments having a molecular weight of about 25,000.

The antibody or fragments thereof can be provided with radioactive labels by conventional procedures for introducing radioactive isotopes into protein molecules. It is desirable to keep the amount of protein injected intravenously low, within the range of 10–250 μg, preferably 10 to 100 μg, in order to avoid possible allergic reaction. For optimum definition and ease of measurement, it is desirable to employ for the label an isotope having a specific gamma-radioactivity of approximately 250 Kev. Iodine isotopes can be employed, the radioiodination being performed by the lactoperoxidase procedure of Marchalonis, Biochem. J. Vol. 113, pages 299–305 (1969). both iodine $^{125}$I and iodine $^{131}$I can be used, the latter being preferred because of its higher radiation energy. There can also be used as labels isotopes of Br and In or other radionuclides having suitable gamma ray energies for imaging.

Radioactive labelled fragments of antibody are preferred over the radioactive labelled antibody itself for the purposes of the present invention because the lower molecular weight facilitates entry of the fragments into, and specific absorption thereof by ischemically damaged intracellular tissue.

The composition used for intravenous injection comprises the radioactive labelled antibody or antibody fragment in any physiologically acceptable injection vehicle such as the aqueous medium in which the product is prepared, as described below, or normal saline or isotonic salt solution. The concentration of the antibody protein or of the antibody fragment is not critical and may vary from 25 to 500 mg./ml. of the total composition to be injected.

Following intravenous injection, the labelled antibody or antibody fragment is carried by the blood stream to the site of the myocardial infarction, where it is specifically absorbed in the ischemically damaged intracellular tissue. Measurement of radiation intensity and location with reference to the heart by observations with counters or through the use of an anger (gamma ray) camera or analogous device, externally of the body at various locations in the vicinity of the heart makes it possible to determine, within a few hours after injection, the location and size of the infarcted region.

The following specific examples will serve to illustrate more fully the nature of the invention without acting as a limitation upon its scope.

EXAMPLE

Cardiac myosin was isolated from canine left ventricular myocardium according to the procedure of Katz et al., Circ. Res. Vol. 19, 611–620 (1965). The myosin was further purified by ammonium sulfate precipitation (37–42% saturation) as described by Wikman-Coffelt et al., Biochem. Biophys. Res. Commun. Vol 51, No. 4, 1097–1104 (1973). The myosin obtained was solubilized in 0.5M KCL, then dialyzed against 40 volumes of 0.15M potassium phosphate pH 7.5, 10mM ethylenediaminetetraacetic acid (Ethylene Dinitrolene Tetraacetate) for 24 hr. Particulate materials were removed by centrifugation at 100,000 g for 30 minutes at 4° C. Homogeneity of the myosin was determined by SDS gel electrophoresis in a discontinuous buffer system as described by Neville, J. Biol. Chem. Vol. 246, 6328–6334 (1971) using 10% polyacrylamide gels. The preparation was found to have two myosin light and one myosin heavy chain bands and slight traces of actin. The purified solution containing canine cardiac myosin (0.5 mg./ml.) was emulsified in an equal volume of complete Freund's adjuvant and injected intradermally and into the toe pads of three New Zealand white rabbits according to the schedule of Lawrence et al., Immunochemistry Vol. 9, 41–49 (1972). The primary immunization consisted of 500 μg of canine cardiac myosin per rabbit, followed 3 weeks later by secondary immunization with 400 μg of myosin. At the fifth week, a booster injection of 300 μg was given. One week later 50 ml of blood was obtained from each animal by ear artery incision. Weekly bleedings were subsequently obtained and booster injections of 500 μg myosin per animal in complete Freund's adjuvant were administered intradermally monthly for 12 months.

The blood specimens from the rabbits were clotted and the antiserum separated by conventional procedure. Antibody activity was determined by measuring the binding capacity of the antiserum for canine cardiac myosin labelled with iodine $^{125}$I by the lactoperoxidase method of Marchalonis, supra. Normal immunoglobulin from untreated rabbits was used as a control.

The antibody content of the antiserum was purified by adding to a 50 ml. aliquot of the antiserum, 25 ml. of saturated ammonium sulfate solution with constant stirring to give a final 33% saturation. The precipitate was separated by centrifugation at 10,000 g for 15 minutes at 4° C., then dissolved in 30mM KCl, 25mM Tris-HCl pH7.5, 1mM EDTA, hereinafter called Tris-buffer and dialyzed through a regenerated cellulose membrane against 40 volumes of Tris-buffer at 4° C. for 24 hr. The protein solution containing the antimyosin antibody was then subjected to affinity chromatography using a column prepared by coupling purified canine cardliac myosin to agarose beads (Sepharose-4B) activated with cyanogen bromide by the general procedure of Cuatrecasas, J. Biol. Chem. 245, 3059–3065 (1970) and equilibrating the immunoadsorbent in Tris-buffer.

After application of the antibody sample, the column was washed with Tris-buffer until the eluate showed no absorbance at 280nm. Myosin-specific antibody was then desorbed with 5M guanidine-HCl, the elution profile being shown in FIG. 1. Fractions containing the antibody were pooled and then dialyzed against 40 volumes of Tris-buffer at 4° C. for 24 hr. Small amounts of insoluble material were removed by centrifugation at 10,000 g for 30 minutes at 4° C. The supernatant solution was then concentrated by vacuum dialysis, using a regenerated cellulose membrane, to approximately 2 mg./ml. as determined by absorbance at 280nm. The antimyosin antibody solution was stored at −20° C. The elution profile of a typical affinity chromatography run on 2.5×70cm myosin-Sepharose column is shown in FIG. 1.

A portion of the purified antibody solution prepared as described above was subjected to hog pepsin (Sigma) digestion at 37° C. for 20 hr at an enzyme to substrate concentration ratio of 1:100, according to the procedure described by Edelman and Marchalonis, Methods in Immunology and Immunochemistry, Vol. I, pp. 422–423, (Academic Press, 1967). At the end of the incubation period, the reaction mixture was centrifuged at 10,000 g for 30 minutes. The supernatant solution was then submitted to agarose (Sephadex G-100) column chromatography (2.5×70cm). Intact antimyosin antibody and protein aggregates were eluted in the void volume. The first protein peak to be eluted in the included volume, comprising approximately 80–90% of the total protein applied to the column, contained the (Fab')$_2$ components of antimyosin antibody, which were concentrated by vacuum dialysis to approximately 2 mg./ml. as described previously above for the antibody solution.

Corresponding fragments of normal rabbit gamma globulin were also prepared as a control in a manner identical to that described above.

Other low molecular weight fragments of the antibody can be prepared by conventional procedures.

Radioiodination of the intact antimyosin antibody and of its (Fab')$_2$ fragments prepared as described above was carried out by the lactoperoxidase procedure of Marchalonis, Biochem. J. Vol. 113, 299–305 (1969), using carrier-free $^{125}$I. Control samples of (Fab')$_2$ fragments of normal immunoglobulin were radioiodinated using carrier-free $^{131}$I by the same method. Covalently bound labeled iodine was separated from free radioiodine by gel permeation chromatography using a 0.5×10cm column of agarose (Sephadex G-25) beads which had been pre-coated with 1.5 ml. of 1% BSA in 0.3M PBS in order to reduce non-specific binding of radioiodinated antibody to the column matrix. The radioiodinated proteins were eluted in the void volume, and were stored at −20° C. The specific activity of radioiodinated antimyosin antibody and of its (Fab')$_2$ fragments was approximately 130 Ci/mM. Both the intact antibody and its fragments can be radioiodinated with $^{131}$I by the same procedure.

Mongrel dogs (19–22 Kg) were anesthetized with intravenous pentabarbital (30 mg/Kg) after which a left thoracotomy was performed under sterile conditions. Acute myocardial infarction was produced employing the method described by Beller et al., Circulation, Vol. 46, 572 (1972). Confluent branches of the left anterior descending coronary artery were ligated 5 minutes apart until approximately 30–50% of the anterolateral wall appeared cyanotic. Coronary venous branches remained intact. Any dogs developing ventricular fibrillation (10%) were not included in the study. An indwelling cannula was inserted in the left atrium via a stab wound in the left atrial appendage in those dogs receiving microspheres for regional blood flow determination. The thoracotomy was then closed and the animals were allowed to recover from anesthesia. All animals alive for more than 24 hr received a 250mg daily dose of ampicillin. All these animals appeared healthy and active during recovery. The left atrial catheter was flushed several times daily with heparinized saline. Radioiodinated antimyosin antibody or (Fab')$_2$ fragments prepared as described above were injected intravenously 4 hr after coronary occlusion in groups of dogs. Each animal received 100μCi of intact antimyosin antibody or (Fab')$_2$ fragments, injected through a disposable Swinnex-13 filter unit (0.22μ pore size) which had been pre-flushed with 5ml of 1% BSA in 0.3M PBS. The amount of radioactive protein received by each animal was 50 to 100μg.

Sacrifice of the dogs was carried out from 24 to 72 hours after coronary occlusion to obtain myocardial samples (0.5–1.0g) of epicardial and endocardial layers of the center and periphery of the infarct, the adjacent border zone region, and normal posterior left ventricular myocardium were obtained. Concentration of radioiodinated material in each sample was determined by gamma scintillation counting and counts per minute per gram wet weight of the samples calculated.

The relative antimyosin antibody or (Fab')$_2$ concentration ($[Ab_I]/[Ab_N]$) in these samples was calculated as the ratio of $^{125}$I labeled antimyosin antibody or (Fab')$_2$ in the infarcted myocardium (I) to that present in normal posterior left ventricular myocardium (N).

In another group of experimentally infarcted dogs 100μCi each of $^{125}$I labeled antimyosin (Fab')$_2$ fragments and Iodine-131 labeled normal rabbit IgG (Fab')$_2$ fragments were simultaneously administered via the intravenous route 4 hr after coronary occulusion. Forty-eight to 72 hr later the animals were sacrificed, and $^{125}$I and $^{131}$I activities in multiple myocardial tissue samples determined by differential spectrometry. The specific localization of antimyoson (Fab')$_2$ fragments was calculated as the difference between relative antimyosin (Fab')$_2$ concentration and relative normal IgG (Fab')$_2$ concentration in the same tissue sample, utilizing the following equation:

Specific Localization = $([Ab_I]/[Ab_N]) - ([IgG_I]/[IgG_N])$.

Figure 2:
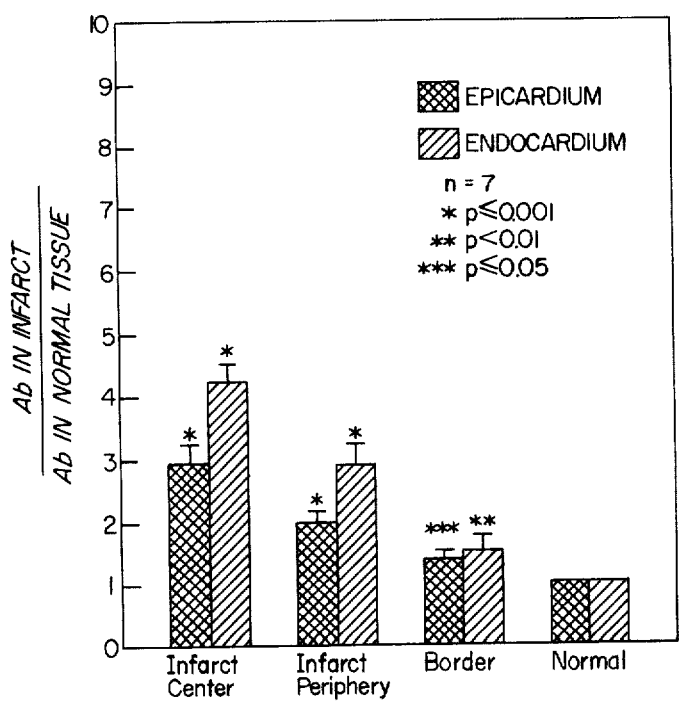
FIG. 2 is a graphical representation of the relative antibody uptake, 24 hours after coronary occulusion, per unit weight of endocardial and epicardial layers from the infarct center, periphery, border zone region, and from a normal myocardium of 7 dogs. One S.E.M. above and below the mean is depicted at the top of each bar.
Figure 3:
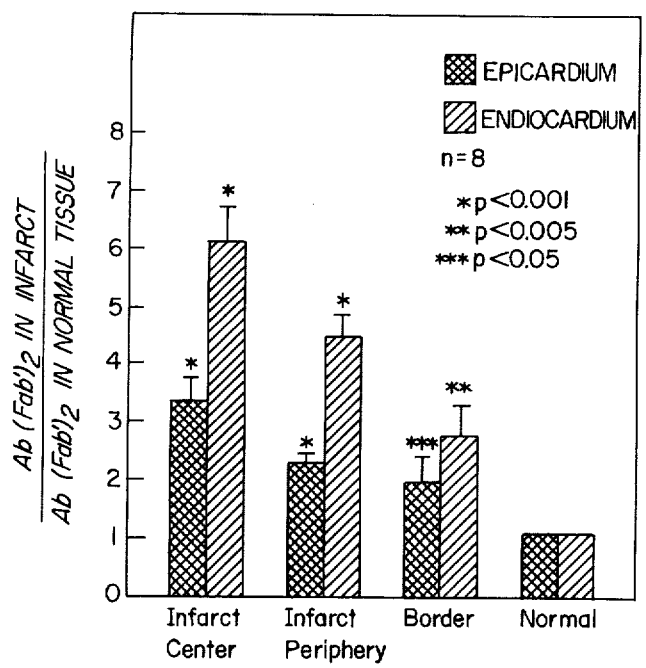
FIG. 3 is a graphical representation similar to FIG. 2 showing the uptake of antibody fragment (Fab')$_2$.
Figure 4:
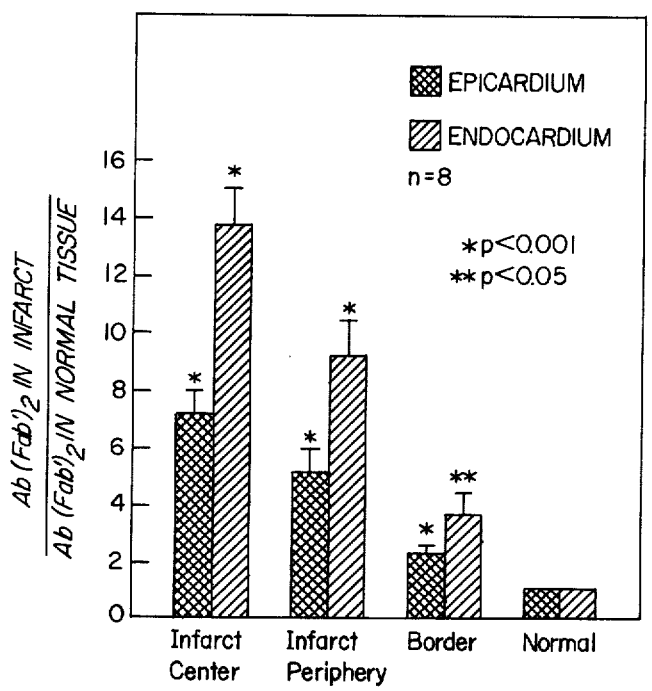
FIG. 4 is a graphical representation similar to FIG. 2 showing uptake of antibody fragment (Fab')$_2$ 72 hours after coronary occlusion.

The results are summarized graphically in FIGS. 2–4 of the drawing which show significant and readily detectable localization of iodine $^{125}$I labeled antibody (FIG. 2) and antibody fragments (FIGS. 3 and 4) in the center and periphery of the infarct. The uptake of the lower molecular weight (Fab')$_2$ fragment in the infarct was significantly greater than that of the whole antibody after the same time for equilibration, i.e., 24 hours after coronary occlusion. When equilibration time was extended to 72 hours, the effect was even more pronounced, as can be seen by comparing the results shown in FIG. 4 with those in FIG. 3. In addition, the use of (Fab')$_2$ fragments eliminated the involvement of complement mediated reactions.

Simultaneous injection of radioiodine labeled antimyosin (Fab')$_2$ fragments and radioiodine labeled normal immunoglobulin (Fab')$_2$ fragments showed, upon dissection, that non-specific trapping of the normal immunoglobulin fragments was 38% of the total relative antimyosin (Fab')$_2$ uptake in the center of the infarct zone, thus demonstrating that it is primarily the specific antigen-antibody interaction which is effective to produce the results of the present invention. Surprisingly, it was found that antibody fragment uptake was greatest in regions of the myocardial tissue where blood flow was most severely reduced.

Similar results can be obtained using cardiac myosin from other sources to produce the antibody and fragments thereof.

What is claimed is:

1. A composition comprising a physiologically acceptable injection vehicle and a member of the group consisting of radioactive labelled antibody for cardiac myosin and radioactive labelled lower molecular weight fragments of said antibody.

2. A composition as claimed in claim 1 in which said fragments are selected from the group consisting of (Fab')$_2$, (Fab')$_1$, and (Fv).

3. A composition as claimed in claim 1 in which said member is radioactive labeled lower molecular weight fragment (Fab')$_2$.

4. The method of determining the location and size of myocardial infarction which comprises injecting intravenously after coronary occlusion an amount of the composition claimed in claim 1 to provide radioactive emissions detectable externally of the body, then measuring the intensity and location of radioactive emissions with reference to the heart.

5. The method of determining the location and size of myocardial infarction which comprises injecting intravenously after coronary occlusion an amount of the composition claimed in claim 2 to provide radioactive emissions detectable externally of the body, then measuring the intensity and location of radioactive emissions with reference to the heart.

6. The method of determining the location and size of myocardial infarction which comprises injecting intravenously after coronary occlusion an amount of the composition claimed in claim 3 to provide radioactive emissions detectable externally of the body, then measuring the intensity and location of radioactive emissions with reference to the heart.

* * * * *